US 6,544,206 B1

(12) United States Patent
Johnston, Jr.

(10) Patent No.: US 6,544,206 B1
(45) Date of Patent: Apr. 8, 2003

(54) DIALYSIS ACCESS SYSTEM AND METHOD

(76) Inventor: Robert H. Johnston, Jr., 303 Pasadena, Victoria, TX (US) 77904

( * ) Notice: Subject to any disclaimer, the term of this patent is extended or adjusted under 35 U.S.C. 154(b) by 88 days.

(21) Appl. No.: 09/687,874

(22) Filed: Oct. 13, 2000

Related U.S. Application Data

(60) Provisional application No. 60/159,628, filed on Oct. 14, 1999.

(51) Int. Cl.[7] .................................................. A61M 1/14
(52) U.S. Cl. ...................... 604/4.01; 210/646; 604/6.07; 604/6.16; 604/28; 604/43; 604/175; 604/256; 604/269
(58) Field of Search ................................ 210/646, 651, 210/782; 604/4.01, 5.01, 5.04, 6.01, 6.07, 6.16, 28, 43, 96.01, 174, 175, 256, 264, 266, 98.01, 269, 915

(56) References Cited

U.S. PATENT DOCUMENTS

| | | | | |
|---|---|---|---|---|
| 4,140,126 A | * | 2/1979 | Choudhury | 604/175 |
| 4,311,587 A | | 1/1982 | Nose et al. | 210/136 |
| 4,456,000 A | * | 6/1984 | Schjeldahl et al. | 604/4.01 |
| 4,578,063 A | | 3/1986 | Inman et al. | 604/175 |
| 4,668,222 A | * | 5/1987 | Poirer | 604/175 |
| 4,822,341 A | * | 4/1989 | Colone | 604/175 |
| 4,936,826 A | | 6/1990 | Amarasinghe | 604/52 |
| 5,312,344 A | * | 5/1994 | Grinfeld et al | 604/101.05 |
| 5,509,897 A | | 4/1996 | Twardowski et al. | 604/43 |
| 5,624,413 A | * | 4/1997 | Markel et al. | 604/175 |
| 5,678,570 A | * | 10/1997 | Manning | 604/4.01 |
| 5,697,905 A | * | 12/1997 | D'Ambrosio | 604/28 |
| 5,702,368 A | * | 12/1997 | Stevens et al. | 604/4.01 |
| 5,704,915 A | | 1/1998 | Melsky et al. | 604/175 |
| 5,776,111 A | * | 7/1998 | Tesio | 604/174 |
| 5,807,311 A | * | 9/1998 | Palestrant | 604/28 |
| 5,931,801 A | | 8/1999 | Burbank et al. | 604/4.01 |
| 5,989,206 A | * | 11/1999 | Prosl et al. | 604/5.01 |
| 5,989,213 A | * | 11/1999 | Maginot | 604/28 |
| 6,083,215 A | * | 7/2000 | Milavetz | 604/4.01 |
| 6,102,884 A | * | 8/2000 | Squitieri | 604/6.01 |
| 6,152,141 A | * | 11/2000 | Stevens et al. | 604/4.01 |
| 6,177,049 B1 | * | 1/2001 | Schnell et al. | 604/4.01 |
| 6,210,365 B1 | * | 4/2001 | Afzal | 604/4.01 |
| 6,231,541 B1 | * | 5/2001 | Kawamura | 604/175 |
| 2002/0169413 A1 | * | 11/2002 | Keren et al. | 604/101.03 |

FOREIGN PATENT DOCUMENTS

WO   WO 97/17102   5/1997   .......... A61M/37/00

* cited by examiner

Primary Examiner—George L. Walton
(74) Attorney, Agent, or Firm—Robert H. Johnston, III

(57) ABSTRACT

A method of and system for providing vascular access in a patient for hemodialysis involves attaching the distal end of an access catheter to the abdominal aorta of the patient and the proximal end of the access catheter to a portion of the patient to allow selective access to an interior portion of the access catheter. A blood-withdrawal catheter and a blood-return catheter are placed into the access catheter until their distal ends are in the patients abdominal aorta and blood may be removed and return to the aorta. When finished, the blood catheters are removed. Selective access to the proximal end of the access catheter is provided, preferably, by a cutaneous port assembly that includes a screwable cap and anti-infection cuff.

10 Claims, 3 Drawing Sheets

DIALYSIS ACCESS SYSTEM AND METHOD

RELATED APPLICATIONS

This application claims the benefit of U.S. Provisional Application Serial No. 60/159,628, filed Oct. 14, 1999.

TECHNICAL FIELD OF THE INVENTION

The present invention relates generally to the design and use of medical devices, and more particularly, to a dialysis access system and method.

BACKGROUND OF THE INVENTION

Access to a patient's vascular system is necessary for a number of treatments such as hemodialysis, which is one of the most critical treatments, and other extra extracorporeal procedures. Hemodialysis, which is used for treatment of end-stage renal disease, involves connecting a patient to a dialysis or kidney machine. The dialysis machine cleanses the patient's blood of waste products such as urea and potassium. Many patients must have this procedure done three or more times per week for the remainder of their lives.

Access to the patient's vascular system for the purpose of withdrawing blood to be delivered to the dialysis machine and returning the dialyzed blood to the patient poses many challenges. A number of procedures have been used for this purpose. One method for chronic hemodialysis access is to create an arteria-venous fistula in the arm of a patient. With the fistula, which is a surgical connection of an artery to a vein, a number of changes occur. The connection bypasses flow-resistant capillaries to provide increased blood flow and the vein is caused to enlarge its diameter and the walls to thicken. Fistulas frequently last only about six months or so before clotting. Sometimes they can be de-clotted, but they remain problematic. Considerable resources are expended to keep such access systems in place and operating properly.

A fistula may not always be used because the patient's blood vessels are not suitable for one reason or another. In such a case, a vascular graft may be used, which is essentially an artificial vessel applied between the artery and the vein. Thrombus or blood clots may partially or wholly occlude both of these approaches. Such blockage limits the blood flow for dialysis and reduces effectiveness of the process. Another problem is that the fistula or graft may become infected. An external catheter may be used temporarily in such situations, but again there are problems with infection and partial occlusion.

Another approach to providing access is to provide an implantable vascular access port at the proximal end of a catheter. With this approach, the connection of the dialysis machine to the patient can be made subcutaneously. Typically, these ports include a chamber and an access region, such as a septum, where the chamber is attached to an implanted catheter that in turn is secured to a blood vessel. In the case of veins, the catheter is typically an indwelling type. And in the case of arteries, the catheter may be attached by anastomosis. These too pose problems including the problem of clotting, venous occlusion, infection, septocpua and possible vein perforation.

SUMMARY OF THE INVENTION

Therefore, a need has arisen for a vascular access system and method that address shortcomings of previous systems and methods. According to an aspect of the present invention, a method of providing vascular access in a patient for hemodialysis that includes the steps of attaching the distal end of an access catheter to the abdominal aorta of the patient; attaching the proximal end of the access catheter to a portion of the patient to allow selective access to an interior portion of the access catheter; and wherein the access catheter is sized and configured to receive a blood-withdrawal catheter into the interior portion of the access catheter until the distal end of the withdrawal catheter is within the patient's abdominal aorta and similarly a blood-return catheter.

According to another aspect of the present invention, a hemodialysis system for performing a hemodialysis treatment on a patient having an access catheter with the distal end of the access catheter coupled to the patient's abdominal aorta and the proximal end coupled near an exterior portion of the patient for gaining selective access to an interior portion of the access catheter; a blood-withdrawal catheter disposed at least in part in the interior portion of the access catheter with the distal end of the withdrawal catheter in the patient's abdominal aorta; a blood-return catheter disposed at least in part in the interior portion of the access catheter with the distal end of the blood return catheter in the patient's abdominal aorta; and a hemodialysis machine fluidly coupled to the proximal end of the blood-withdrawal catheter and fluidly coupled to the proximal end of the blood-return catheter. According to another aspect of the present invention, a cutaneous port assembly is coupled to the proximal end of the access catheter for allowing selective access to the interior of the access catheter.

According to another aspect of the present invention, a method of performing a hemodialysis treatment in a patient having a vascular access system includes the steps of gaining access to an interior portion of an access catheter extending between a location near the patient's exterior and the patient's abdominal aorta; placing a blood-withdrawal catheter into an interior portion of the access catheter until a distal end of the blood-withdrawal catheter is within the patient's abdominal aorta; placing a blood-return catheter into the interior portion of the access catheter until a distal end of the blood-return catheter is within the abdominal aorta; fluidly coupling a proximal end of the of the blood-withdrawal catheter to a hemodialysis machine; fluidly coupling a proximal end of the of the blood-return catheter to the hemodialysis machine; and performing hemodialysis with the hemodialysis machine with blood being removed from the patient through the blood-withdrawal catheter and returned through the blood-return catheter.

An advantage of the present invention is that it provides a convenient, high-blood flow access for hemodialysis. Another advantage of the present invention is that the access system will not have conduits susceptible to clotting that are directly used in the removal or return of blood for dialysis. The system and method provide for high flow that does not depend on the flow through a graft per se, but only as a conduit for hemodialysis catheters to pass through. Another advantage of the present invention is that the system will remain operable with acceptable performance in a patient for long periods of time.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

The preferred embodiment of the present invention and its advantages are best understood by referring to FIGS. 1–4 of the drawings, like numerals being used for like and corresponding parts of the various drawings.

Figure 1:
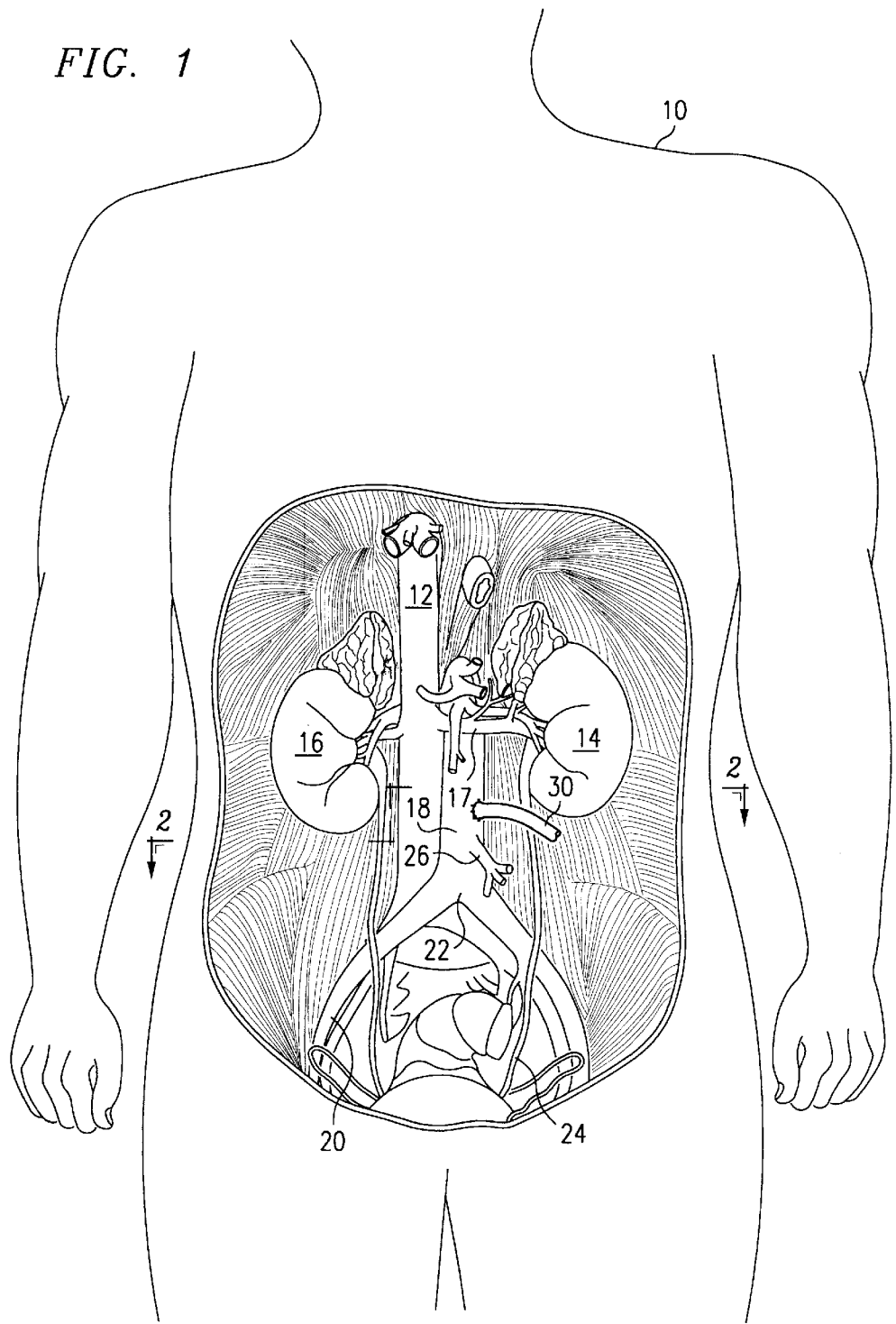
FIG. 1 is a schematic anterior view of a patient's abdominal cavity presenting an aspect of the present invention.

Referring to FIG. 1, an anterior view of the abdominal cavity of a patient 10 is presented with its inferior vena cava 12, left kidney 14, right kidney 16, left renal vein 17, abdominal aorta 18, external iliac 20, aortic bifurcation 22, ureter 24, and inferior mesenteric artery 26. As described further below, an access catheter 30 is attached by astemosis to the abdominal aorta 18.

Figure 2:
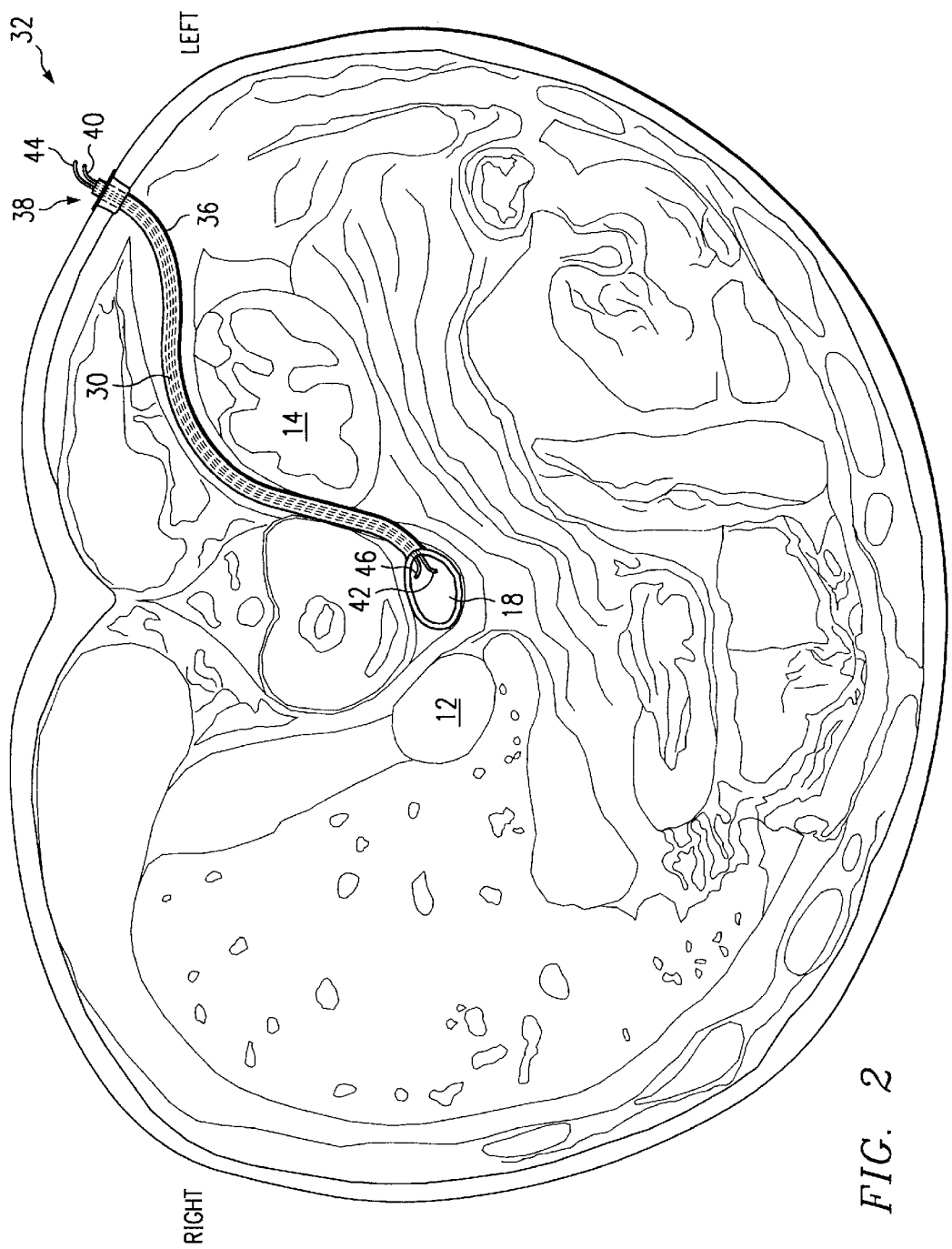
FIG. 2 is a transverse section of the patient of FIG. 1 taken along line 2—2 (the transverse section is taken above the relevant site and the figure is looking down on the section)
Figure 3:
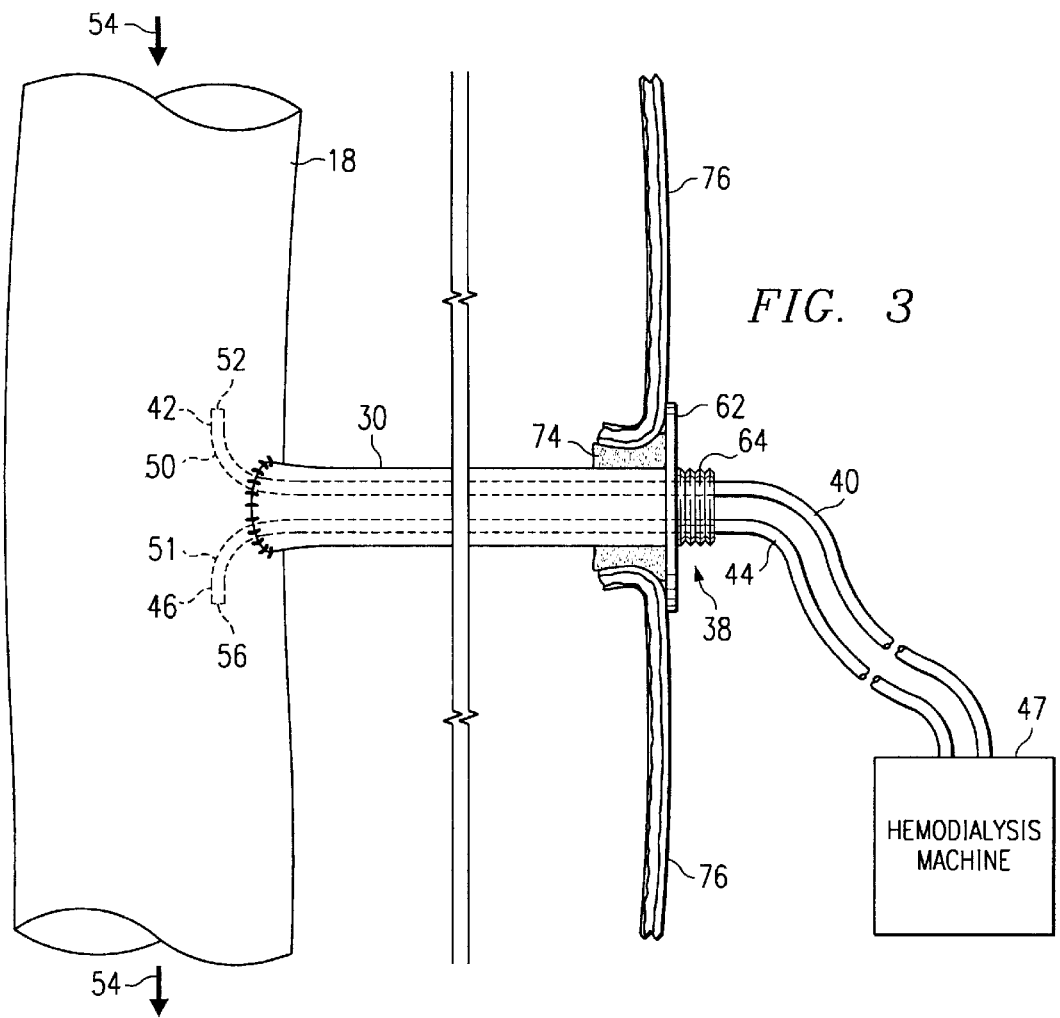
FIG. 3 is a schematic cross-section of an access system in situ according to an aspect of the present invention; and, FIG. 4 is a perspective view of a cutaneous port member according to an aspect of the present invention.

Referring now to FIGS. 2 and 3, hemodialysis access system 32 is shown in situ of patient 10. System 32 includes an access catheter 30 attached at its distal end 34 to abdominal aorta 18. Access catheter 30 may be any type of implantable graft, but a Goretex® graft or PTFE graft is preferred. The proximal end 36 of catheter 30 is secured to the left flank 38 of patient 10 by a cutaneous port assembly 38, which will be described further below. When system 32 is in use, a blood-withdrawal catheter 40 is introduced through cutaneous port assembly 38 into an interior portion of the access catheter 30 such that a distal end 42 of catheter 40 enters abdominal aorta 18. Similarly, a blood-return catheter 44 is introduced into cutaneous port assembly 38 through access catheter 30 such that a distal end 46 of catheter 44 enters abdominal aorta 18. Catheters 40 and 44 are preferably of disposable sterile plastic. In this position, blood may be removed through catheter 40 and delivered to a hemodialysis machine 47 for treatment of the blood and then returned through blood-return catheter 44 to abdominal aorta 18.

Referring to FIG. 3, additional features of system 32 are visible. With catheters 40 and 44 shown in place for a hemodialysis treatment, the distal end 42 of catheter 40 is shown with a curvature 50 and in place with an orientation such that aperture 52,is substantially perpendicular to blood flow 54. Similarly, aperture 56 on distal end 46 of catheter 44 is substantially perpendicular to blood flow 54 such that return blood flows substantially parallel to blood flow 54. A curved portion 51 is formed on the distal end of catheter 46 to preferably be oriented with aperture 56 facing downstream for blood flow 54 in aorta 18.

Figure 4:
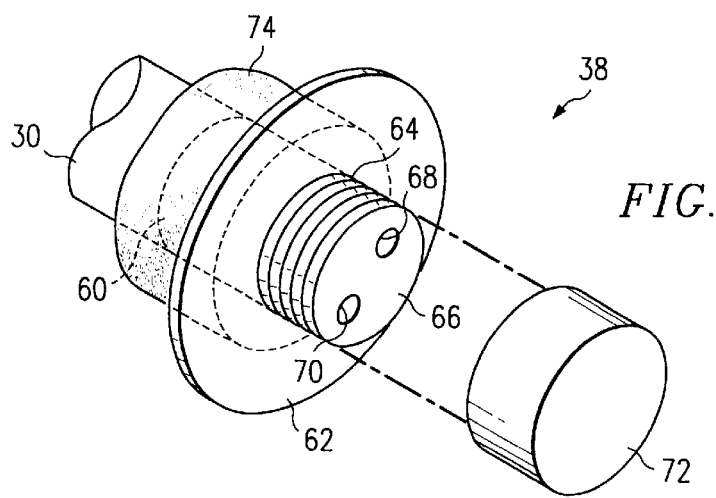

Referring to FIGS. 3 and 4, cutaneous port assembly 38 has a hollow cylindrical member 60 to which access catheter 30 is attached. Cylinder 60 has a shield member or disc 62 attached on an intermediate portion and has threads 64 and an end cap 66 in which first aperture 68 and second aperture 70 are formed. Apertures 68 and 70 are for receiving catheters 40 and 44 respectively. A sealing cap 72 is sized and configured to mate with threads 64 to provide a secure seal over apertures 68 and 70 when system 32 is not in use. An antibiotic cuff or infection avoidance collar 74 is disposed adjacent to shield member 62 and preferably around the proximal end of access catheter 30. Infection avoidance collar or antibiotic cuff 74 is an antibiotic impregnated material such Dacron to prevent infection. Thus, as shown best in FIG. 3, cutaneous port assembly 38 provides access through the patient's skin 76. Port assembly 38 may take numerous forms and shapes that provide convenient access to an interior portion of the access catheter 30, but a subsystem with a removable cap an anti-infection cuff is preferred.

With reference to FIGS. 1 through 4, a method for installing access system 32 will be described. A surgeon installs access system 32 by gaining access to abdominal aorta 18 through an incision preferably on the left flank between the iliac crest and the ribs. The distal end 34 of catheter 30 is attached by astemosis to aorta 18. The preferred insertion point or attachment point for the distal end of 34 the access catheter 30 is between the renal arteries and the aortic bifurcation—the attachment is roughly between vertebraes L1 and L3. Access catheter 30 is run in the retro-peritoneum space. The proximal end 36 of catheter 30 is sized to terminate at the left flank 38 of patient 10. The proximal end 36 of catheter 30 is placed over a distal portion of cylindrical member 60 and infection avoidance collar 74 is placed over an outer portion of the proximal end of catheter 30. Collar 74 may also be attached to the proximal end before surgery and an intermediate portion of catheter 30 cut to size the length. Cutaneous port assembly 38 is positioned with shield member 62 substantially adjacent with skin 76. Thus system 32 is put into place. When system 32 is not in use, cap 72 is secured on threads 64 to prevent exposure of apertures 68 and 70.

When in use the cap 72 is removed and the end portion 66 is wiped with Betadine and then the sterile access cannulas or catheters 40, 44 are inserted into apertures 68, 70. While clotting or obstruction in catheters 40 and 44 is not believed to be a problem as the internal conduit of catheter 30 is filled with heparine after use. Catheters 40, 44 are attached to dialysis machine 47. Note that the high-pressure access may allow faster dialysis. After dialysis is completed, the catheters 40, 44 are removed and discarded. An anti-coagulant such as heprin is then injected into the interior of access catheter 30 and then cap 72 attached.

If it is desired to ever remove system 32 because of infection or other reason, catheter 30 may be closed on the proximal end and cutaneous port 38 removed. In more extreme cases, the entire system may be removed.

Although the present invention and its advantages have been described in detail, it should be understood that various changes, substitutions and alterations can be made therein without departing from the spirit and scope of invention as defined by the appended claims. For example, components and systems shown in one embodiment may be included in other embodiments.

What is claimed is:

1. A method of providing vascular access in a patient for hemodialysis, the method comprising the steps of:
   providing an access catheter with a proximal end and a distal end;
   attaching the distal end of the access catheter to the abdominal aorta of the patient;
   attaching the proximal end of the access catheter to a portion of the patient to allow selective access to an interior portion of the access catheter;
   providing a blood-withdrawal catheter having a proximal end and a distal end;
   providing a blood-return catheter having a proximal end and a distal end;
   inserting the blood-withdrawal catheter into the interior portion of the access catheter until the distal end of the withdrawal catheter is within the patient's abdominal aorta;

attaching the proximal end of the blood-withdrawal catheter to a dialysis machine;

inserting the blood-return catheter into the interior portion of the access catheter until the distal end of the blood-return catheter is within the patient's abdominal aorta; and attaching the proximal end of the blood-return catheter to the dialysis machine.

2. The method of claim 1 wherein the step of attaching the proximal end of the access catheter to the patient to allow selective access to the interior of the access catheter comprises attaching a cutaneous port assembly to the patient.

3. The method of claim 1 wherein the distal end of the blood-withdrawal catheter is curved and wherein the step of inserting the blood-withdrawal catheter further comprises inserting the blood withdrawal catheter into the abdominal aorta with the curved portion oriented to place an aperture on the distal end of the blood-withdraw catheter so that faces bloodflow in the abdominal aorta.

4. A hemodialysis system for performing a hemodialysis treatment on a patient, the system comprising:

an access catheter having a proximal end and a distal end, the distal end of the access catheter sized and configured for coupling to a patient's abdominal aorta and the proximal end coupled near an exterior portion of the patient for gaining selective access to an interior portion of the access catheter;

a blood-withdrawal catheter having a proximal end and a distal end, the blood-withdrawal catheter sized and configured to be disposed at least in part in the interior portion of the access catheter through the first or second aperture in the end cap and the distal end of the withdrawal catheter sized and configured to be placed in the patient's abdominal aorta;

a blood-return catheter having a proximal end and a distal end, the blood-return catheter sized and configured to be disposed at least in part in the interior portion of the access catheter through the first or second aperture in the end cap and the distal end of the blood return catheter sized and configured to be placed in the patient's abdominal aorta; and a hemodialysis machine fluidly coupled to the proximal end of the blood-withdrawal catheter and fluidly coupled to the proximal end of the blood-return catheter.

5. The system of claim 4 further comprising a cutaneous port assembly coupled to the proximal end of the access catheter for allowing selective access to the interior of the access catheter.

6. The system of claim 4 wherein the distal end of the blood-withdrawal catheter is formed with a curve and the distal end of the blood-return catheter is formed with a curve.

7. A method for gaining access to a patient's blood to perform hemodialysis, the method comprising the steps of:

providing an access catheter formed of an implantable graft and having a distal end and a proximal end;

attaching by astemosis the distal end of the access catheter to the abdominal aorta between the patient's renal arteries and the patient's aortic bifuracation;

providing a cutaneous port assembly, wherein the cutaneous port assembly comprises:

a hollow cylindrical member having a first end, second end, and an intermediate portion therebetween, the cylindrical member for attaching the proximal end of the access catheter, the second end of the cylindrical member formed with threads, a shield member attached to an intermediate portion of the cylindrical member, an end cap coupled to the second end of the cylindrical member, the end cap formed with a first aperture and a second aperture, an infection avoidance collar coupled proximate the first end of the cylindrical member, the collar for facilitating tissue growth and avoiding infection, and a removeable sealing cap having threads and sized and configured to mate with the threads on the second end of cylindrical member and to form a liquid-tight seal when so mated;

attaching the proximal end of the access catheter to the first end of the cylindrical member of the cutaneous port assembly;

providing a blood-withdrawal catheter having a distal end and a proximal end and sized to be inserted into the first or second aperture of the end cap of the cutaneous port assembly;

inserting the distal end of the blood-withdrawal catheter through the first or second aperature of the cutaneous port assembly and into the abdominal aorta of the patient;

providing a blood-return catheter having a distal end and a proximal end and sized to be inserted into the first or second aperture of the end cap of the cutaneous port assembly; and inserting the distal end of the blood-return catheter through the first or second aperture of the cutaneous port assembly and into the abdominal aorta of the patient.

8. The method of claim 7 wherein the step of providing a blood-withdrawal catheter comprises providing a blood-withdrawal catheter having a curved distal end and wherein the step of inserting the blood-withdrawal catheter comprises inserting the distal end of the blood-withdrawal catheter so that the curve of the distal end is toward an upstream position with respect to blood flow.

9. The method of claim 7 wherein the step of providing a blood-return catheter comprises providing a blood-return catheter having a curved distal end wherein the step of inserting the blood-return catheter comprises inserting the distal end of the blood-return catheter so that the curve of the distal end is toward a downstream position with respect to blood flow.

10. The method of claim 7 wherein:

the step of providing a blood-withdrawal catheter comprises providing a blood-withdrawal catheter having a curved distal end;

the step of inserting the blood-withdrawal catheter comprises inserting the distal end of the blood-withdrawal catheter so that the curve of the distal end is toward an upstream position with respect to blood flow;

the step of providing a blood-return catheter comprises providing a blood-return catheter having a curved distal end; and the step of inserting the blood-return catheter comprises inserting the distal end of the blood-return catheter so that the curve of the distal end is toward a downstream position with respect to blood flow.

* * * * *